US006805871B1

(12) United States Patent
Benner et al.

(10) Patent No.: US 6,805,871 B1
(45) Date of Patent: Oct. 19, 2004

(54) COSMETIC AND DERMATOLOGICAL LIGHT PROTECTION FORMULATIONS IN THE FORM OF O/W MACROEMULSIONS OR O/W MICROEMULSIONS CONTAINING SHEA BUTTER

(75) Inventors: Gerhard Benner, Buxtehude (DE); Astrid Heptner, Hamburg (DE); Anja Knüppel, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/723,189

(22) Filed: Nov. 27, 2000

(30) Foreign Application Priority Data

Dec. 1, 1999 (DE) .......................... 199 57 761

(51) Int. Cl.[7] .......................... A61K 7/00; A61K 7/021; A61K 9/107
(52) U.S. Cl. .......................... 424/401; 424/59; 424/489; 514/938
(58) Field of Search .......................... 424/401, 59, 489, 424/47; 514/938, 785

(56) References Cited

U.S. PATENT DOCUMENTS

| 4,661,343 | A | | 4/1987 | Zabotto et al. |
| 4,719,239 | A | * | 1/1988 | Muller et al. ............... 514/785 |
| 5,250,289 | A | | 10/1993 | Boothroyd et al. |
| 5,466,457 | A | | 11/1995 | Schneider et al. |
| 5,589,178 | A | | 12/1996 | Aubert et al. ............... 424/401 |
| 5,750,124 | A | * | 5/1998 | Gohla et al. ............... 424/401 |
| 5,858,334 | A | * | 1/1999 | Ascione et al. ............... 424/59 |
| 5,876,702 | A | | 3/1999 | Gers-Barlag et al. |
| 5,900,231 | A | | 5/1999 | Richard et al. ............... 424/60 |
| 5,993,857 | A | * | 11/1999 | Menzel et al. ............... 424/489 |
| 6,224,850 | B1 | * | 5/2001 | Breton et al. ............... 424/47 |

FOREIGN PATENT DOCUMENTS

| DE | 43 08 282 A1 | 9/1994 |
| EP | 0 836 847 A2 | 4/1998 |
| WO | WO 93/11865 | 6/1993 |
| WO | WO 95/17155 | 6/1995 |

OTHER PUBLICATIONS

Fette und Öle Fettderivate Folgeprodukte; Zeitschrift für die; Fett–, Öl–, Tensid–, Kosmetik–und Pharmaindustrie; 113. Jahrgang, Augsburg, Juni 25. 1987; Nr. 10–2. Juniheft; Schibuter; Helmuth Olberg; pps. 333–334.
W. Skrypzak, A.K. Reng; Technologische Aspekte bei der Herstellung von Emulsionen; Vostrag, gehalten anläßlich der SEPAWA–Jahrestagung am 10. Oktober 1991; SÖFW–Journal, 118, Jahrgang, 5/92; pps. 287–296.
A. K. Reng; Hochschulkurs >> Emulgiertechnik << 1998 Institut für Lebensmittelverfahrenstechnik der Universität Karlsruhe (TH); Karlsruhe, 2.–4. März 1998; SÖFW–Journal, 124. Jahrgang 7/98; pps. 439–443.
G. Kutz, St. Frieβ; Moderne Verfahren zur Herstellung von halbfesten und flüssigen Emulsionen—Eine aktuelle Übersicht–; SÖFW–Journal, 124, Jahrgang 5/98; pps. 308–313.
S. H. Gohla, J. Nielsen; Partial Phase Solu–Inversion Technology (PPSIT); A novel process to manufacture long term stable multiple emulsions by an in situ one step procedure; SÖFW–Journal, 121. Jahrgang, 10/95; pps. 707–713.

* cited by examiner

Primary Examiner—Thurman K. Page
Assistant Examiner—Mina Haghighatian
(74) Attorney, Agent, or Firm—Norris McLaughlin & Marcus PA

(57) ABSTRACT

Sprayable oil-in-water emulsions, in particular O/W microemulsions, comprising inorganic pigments [lacuna] emulsifiers whose lipophilicity is dependent either on the pH or on the temperature, and one or more film formers chosen from the group of silicone emulsifiers.

6 Claims, 4 Drawing Sheets

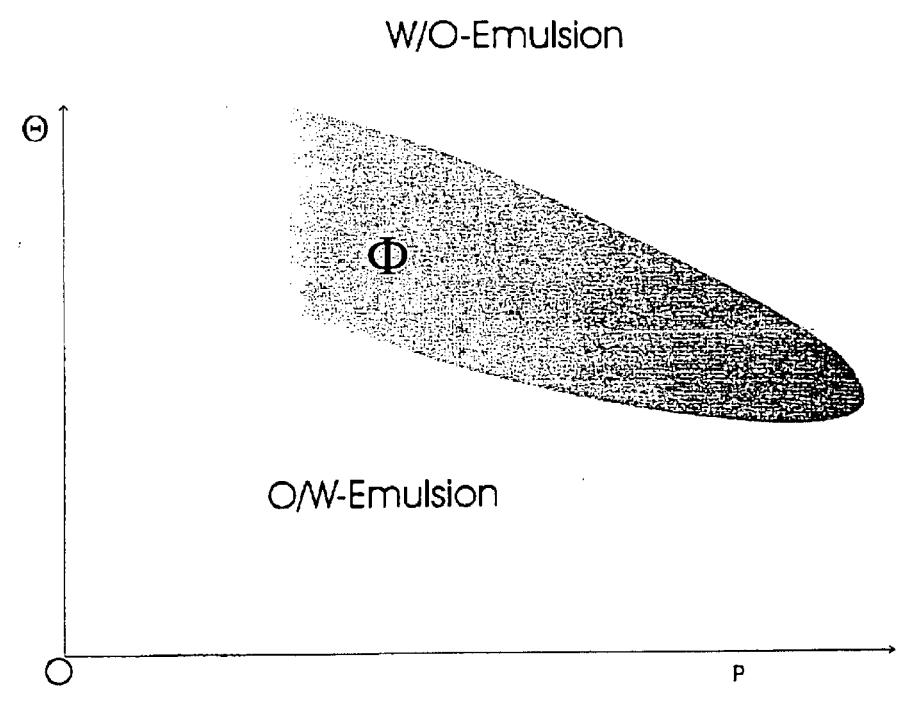

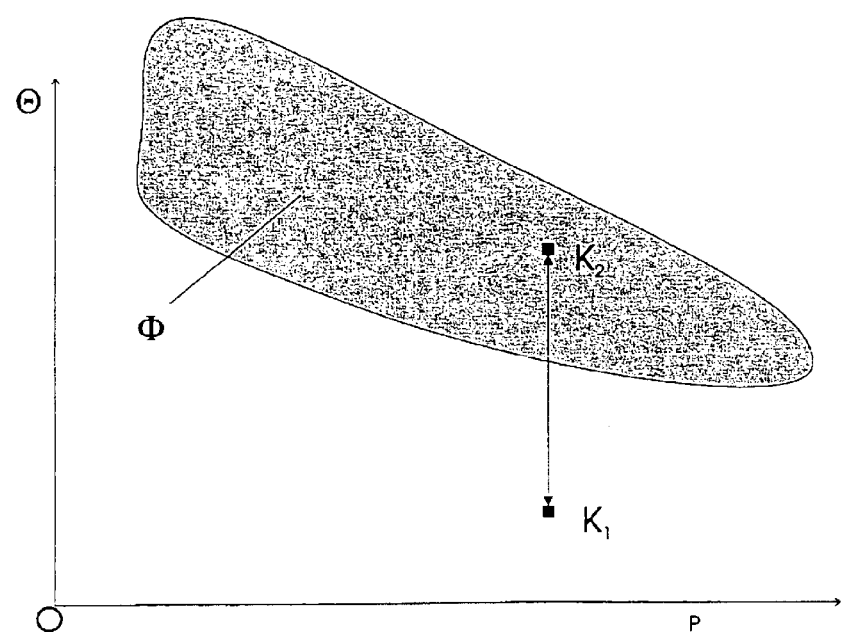

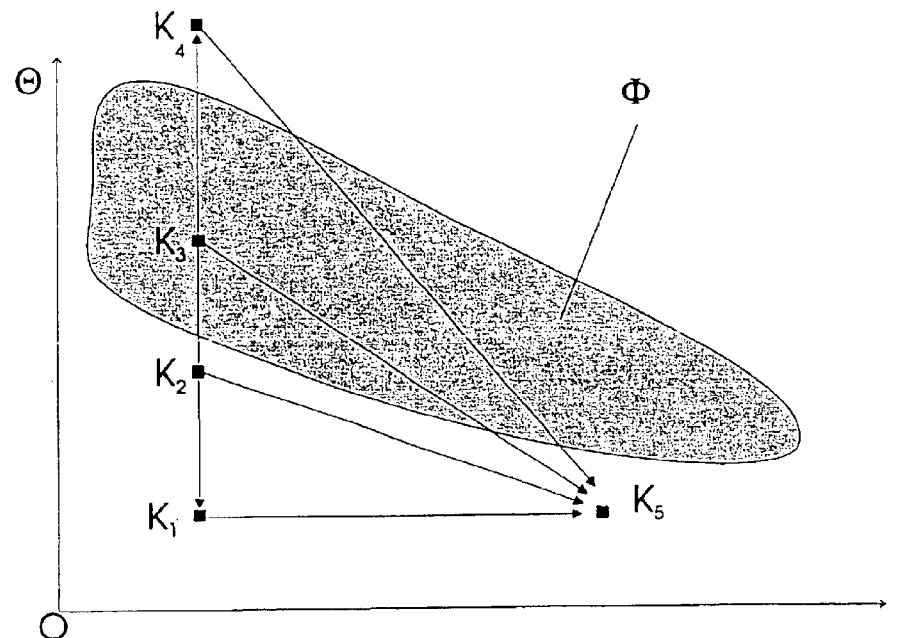

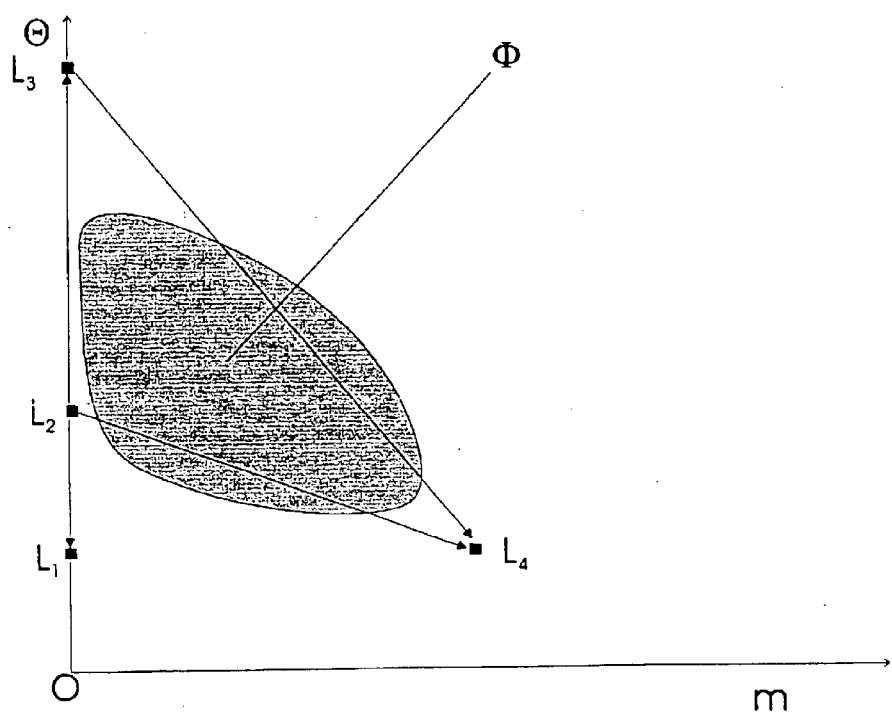

COSMETIC AND DERMATOLOGICAL LIGHT PROTECTION FORMULATIONS IN THE FORM OF O/W MACROEMULSIONS OR O/W MICROEMULSIONS CONTAINING SHEA BUTTER

The present invention relates to cosmetic and dermatological emulsions, in particular skincare cosmetic and dermatological emulsions. In an advantageous embodiment, the present invention relates to a use which permits the preparation of cosmetically elegant preparations, in particular emulsions, having excellent sensory and skincare properties.

The skin is the largest human organ. Amongst its many functions (for example for temperature regulation and as a sensory organ) the barrier function, which prevents the skin (and ultimately the entire organism) from drying out, is doubtless the most important. At the same time, the skin acts as a protective device against the penetration and absorption of external substances. This barrier function is effected by the epidermis, which, as the outermost layer, forms the actual protective sheath against the environment. Being about one tenth of the total thickness, it is also the thinnest layer of the skin.

The epidermis is a stratified tissue in which the outer layer, the horny layer (Stratum corneum), is the part which is of significance for the barrier function. The Elias skin model, which is currently recognized in the specialist-field (P. M. Elias, *Structure and Function of the Stratum Corneum Permeability Barrier, Drug Dev. Res.* 13, 1988, 97–105), describes the horny layer as a two-component system, similar to a brick wall (bricks and mortar model). In this model, the horny cells (corneocytes) correspond to the bricks, and the lipid membrane in the intercellular spaces, which is of complex composition, corresponds to the mortar. This system is essentially a physical barrier to hydrophilic substances, but, because of its narrow and multilayered structure, can equally, however, also only be passed by lipophilic substances with difficulty.

The present invention relates, in a particular embodiment, to cosmetic or pharmaceutical preparations having a reduced feeling of stickiness, to processes for their preparation, and also to the use of active ingredients for reducing the feeling of stickiness of cosmetic preparations.

Apart from its barrier action against external chemical and physical influences, the epidermal lipids also contribute to the holding together of the horny layer and have an effect on the smoothness of the skin. In contrast to the sebaceous gland lipids, which do not form a continuous film on the skin, the epidermal lipids are distributed over the entire horny layer.

The extremely complex interaction of the moisture-binding substances and of the lipids of the upper layers of the skin is very important for the regulation of skin moisture. For this reason, cosmetics generally comprise, in addition to balanced lipid mixtures and water, water-binding substances.

In addition to the chemical composition, however, the physical behavior of these substances is also of importance. The development of very biocompatible emulsifiers and surfactants is therefore desirable. Products formulated therewith aid the liquid-crystalline organization of the intercellular lipids of the Stratum corneum, thereby improving the barrier properties of the horny layer. It is particularly advantageous if their molecular constituents consist of substances which are naturally occurring in the epidermis.

Cosmetic skin care primarily means that the natural function of the skin as a barrier against environmental influences (e.g. dirt, chemicals, microorganisms) and against the loss of endogenous substances (e.g. water, natural fats, electrolytes) is strengthened or rebuilt.

If this function is impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important when the natural regeneration ability is insufficient. Furthermore, skincare products should protect against environmental influences, in particular against sun and wind, and delay skin aging.

Medicinal topical compositions generally comprise one or more medicaments in an effective concentration. For the sake of simplicity, in order to distinguish clearly between cosmetic and medicinal use and corresponding products, reference is made to the legal provisions of the Federal Republic of Germany (e.g. Cosmetics Directive, Foods and Drugs Act).

Customary cosmetic forms of application are emulsions. This term generally means a heterogeneous system of two liquids which are immiscible or miscible only to a limited extent with one another, which are usually referred to as phases. One is in the form of droplets (disperse or internal phase), while the other liquid forms a continuous (coherent or internal) phase. Less common forms of application are multiple emulsions, i.e. those which, in the droplets of the dispersed (or discontinuous) phase, comprise for their part droplets of a further dispersed phase, e.g. W/O/W emulsions and O/W/O emulsions.

More recent findings have recently led to a better understanding of cosmetic emulsions which are of relevance in practice. Here, it is assumed that the emulsifier mixtures used in excess form lamellar liquid-crystalline phases or crystalline gel phases. In the gel network theory, stability and physicochemical properties of such emulsions are attributed to the formation of viscoelastic gel networks.

If the two liquids are water and oil and the oil droplets are finely dispersed in water, then this is an oil-in-water emulsion (O/W emulsion, e.g. milk). The basic character of an O/W emulsion is defined by the water. In the case of a water-in-oil emulsion (W/O emulsion, e.g. butter) the principle is reversed, the basic character being determined here by the oil.

In order to be able to ensure the metastability of emulsions, interface-active substances, i.e. emulsifiers, are usually necessary. The use per se of customary cosmetic emulsifiers is entirely acceptable. Nevertheless, emulsifiers, as ultimately any chemical substance, may in certain cases cause allergic reactions or reactions based on oversensitivity of the user. For example, it is known that in some particularly sensitive people, certain light dermatoses are triggered by certain emulsifiers and simultaneous action of sunlight.

It is possible to prepare emulsifier-free preparations which, for example, have, in an aqueous phase, dispersed oil droplets, similar to an O/W emulsion. A prerequisite for this may be that the continuous aqueous phase has a gel framework which stabilizes the dispersed phase, and other conditions besides. Such systems are sometimes called hydrodispersions or oleodispersions depending on which is the disperse phase and which is the continuous phase.

For cosmetics technology, however, it is neither necessary nor possible to dispense with emulsifiers altogether, especially since there is a certain choice of particularly mild emulsifiers. However, the prior art lacks a satisfactorily broad range of such emulsifiers which would then also significantly broaden the application spectrum of correspondingly mild cosmetic preparations which are tolerated by the skin.

An object of the present invention was therefore to provide cosmetic and dermatological preparations having excellent skincare properties.

A disadvantage, in particular of O/W emulsions, is often their inadequate stability to relatively high electrolyte concentrations, which manifests itself in phase separation. This can indeed sometimes lead to problems, even in the case of W/O emulsions, although this is by no means as important here as in the case of O/W systems. Although these can often be remedied to a certain extent through appropriate choice of the emulsifier system, other disadvantages, however, arise just as often.

On the other hand, it is often desirable to use certain electrolytes in order to be able to utilize their other physical, chemical or physiological properties.

The concentrations of all of the constituents of a cosmetic or dermatological preparation are usually given in units such as % by weight, mol % and the like. In view of their greater or lesser dissociation into cations and anions, often in several dissociation stages, it sometimes appears more advantageous, for the description of the present invention and its technical background, to start from the ionic strength of a given electrolyte in its solution.

The ionic strength I of an electrolyte solution is defined as $$I = \frac{1}{2}\sum_i c_i z_i^2$$

where $c_i$ are the concentrations of the individual types of ion (in mol/l) and $z_i$ are their charges. The physical unit of ionic strength is that of a concentration (mol/l).

For example, a 1% strength (=0.17 molar) sodium chloride solution has an ionic strength I=0.17.

Another object of the present invention was therefore to discover ways of producing cosmetic or dermatological emulsions, in particular O/W emulsions, which are stable to increased electrolyte concentrations—or increased ionic strengths.

The person skilled in the art is naturally aware of a large number of ways of formulating stable O/W preparations for cosmetic or dermatological use, for example in the form of creams and ointments, which are spreadable in the range from room temperature to skin temperature, or as lotions and milks, which are more likely to be flowable in this temperature range. However, there are only a few formulations in the prior art which are of sufficiently low viscosity that they would, for example, be sprayable.

In addition, low-viscosity preparations of the prior art frequently have the disadvantage that they are unstable, and are limited to a narrow field of application or to a limited choice of feed material. Low-viscosity products in which, for example, highly polar oils—such as the vegetable oils otherwise frequently used in commercially available products—are sufficiently stabilized are therefore currently not on the market.

The term "viscosity" means the property of a liquid to resist the mutual laminar displacement of two neighboring layers (internal friction). This so-called dynamic viscosity is nowadays defined according to $\eta=t/D$ as the ratio of shear stress to the velocity gradient perpendicular to the direction of flow. For Newtonian liquids, $\eta$ is a material constant having the SI unit Pascal second (Pa·s) at a given temperature.

The quotient $v=\eta/\rho$ from the dynamic viscosity $\eta$ and the density $\rho$ of the liquid is referred to as the kinematic viscosity $v$ and is given in the SI unit m$^2$/s.

Fluidity ($\phi$) is the inverse of viscosity ($\phi=1/\eta$). In the case of ointments and the like, the use value is codetermined by the so-called tack. The tack of an ointment or ointment base or the like means its property to draw threads of varying lengths when a small sample is removed; accordingly, a distinction is made between short- and long-stretch substances.

While the graphical representation of the flow behavior of Newtonian liquids at a given temperature produces a straight line, in the case of so-called non-Newtonian liquids considerable deviations often arise, depending on the particular velocity gradient D (shear rate $\gamma$) or the shear stress $\tau$. In these cases, the so-called apparent viscosity can be determined which, although not bound to the Newtonian equation, can be used to determine the true viscosity values by graphical methods.

Falling body viscometry is suitable only for investigating Newtonian liquids and gases. It is based on Stokes' law, according to which, for the falling of a sphere through a liquid which flows around it, the dynamic viscosity $\eta$ can be determined from $$\eta = \frac{2r^2(\rho_K - \rho_{Fl})\cdot g}{9\cdot v}$$

where r=radius of the sphere, v=fall velocity, $\rho_K$=density of the sphere, $\rho_{Fl}$=density of the liquid and g=acceleration of the fall.

O/W emulsions with a low viscosity which have a storage stability as is required for marketable products can only be formulated in accordance with the prior art in a very complex manner. Accordingly, the supply of such formulations is extremely low. Nevertheless, formulations of this type could offer the consumer hitherto unknown cosmetic results.

An object of the present invention was to make available preparations which have very low viscosity and do not have the disadvantages of the prior art.

For polyol fatty acid esters, the definition of the HLB value is given by the formula I $$HLB=20*(1-S/A)$$

For a group of emulsifiers whose hydrophilic moiety consists only of ethylene oxide units, the formula II applies

| HLB = E/5 | | |
|---|---|---|
| where | S | = saponification number of the ester, |
| | A | = acid number of the recovered acid, |
| | E | = mass fraction of ethylene oxide (in %) based on the overall molecule. |

Emulsifiers with HLB values of 6–8 are generally W/O emulsifiers, and those with HLB values of 8–18 are generally O/W emulsifiers.

Reference: "Kosmetik—Entwicklung, Herstellung und Anwendung kosmetischer Mittel" [Cosmetics—Development, Preparation and Use of Cosmetic Compositions], W. Umbach (Ed.), Georg Thieme Verlag 1988.

Hydrophilic emulsifiers (with high HLB values) are generally O/W emulsifiers. Accordingly, hydrophobic or lipophilic emulsifiers (with low HLB values) are generally W/O emulsifiers.

U.S. Pat. No. 4,931,210 describes a process for the preparation of W/O/W emulsions where polyglycerol polyricinoleates are used as emulsifiers.

The droplet diameters of customary "simple", i.e. non-multiple emulsions are in the range from about 1 $\mu$m to about 50 $\mu$m. Such "macroemulsions" are, without further coloring additives, milky-white in color and opaque. Finer "macroemulsions", the droplet diameters of which are in the range from about $10^{-1}$ $\mu$m to about 1 $\mu$m are, again without coloring additives, bluish-white in color and opaque. Such "macroemulsions" usually have high viscosity.

It is only micellar and molecular solutions having particle diameters of less than about $10^2$ $\mu$m, but which are no longer to be regarded as true emulsions, which have a clear and transparent appearance.

By contrast, the droplet diameter of microemulsions is in the range from about $10^{-2}$ $\mu$m to about $10^{-1}$ $\mu$m. Microemulsions are translucent and in most cases of low viscosity. The viscosity of many microemulsions of the O/W type is comparable with that of water.

The advantage of microemulsions is that, in the disperse phase, active ingredients can be present in essentially more finely dispersed form than in the disperse phase of "macroemulsions". A further advantage is that they are sprayable as a result of their low viscosity. If microemulsions are used as cosmetics, corresponding products are characterized by high cosmetic elegance.

It is known that hydrophilic emulsifiers change their solubility behavior from water-soluble to fat-soluble with increasing temperature. The temperature range in which the emulsifiers have changed their solubility is called the phase inversion temperature range (PIT).

T. J. Lin, H. Kurihara and H. Ohta (Journal of the Society of Cosmetic Chemists 26, pp. 121–139, March 1975) show that for nonpolar oils extremely unstable multiple emulsions may be present in the PIT range.

The object of the present invention was therefore to remedy these shortcomings.

It was furthermore an object of the present invention to make available preparations which significantly improve the condition of the skin, in particular reduce skin roughness.

It is admittedly known that certain substances, for example a few selected powder raw materials, in particular talc, can be added to reduce a feeling of stickiness and also a feeling of greasiness. However, apart from the fact that this is only rarely completely successful, such an addition also changes the viscosity of the product in question and lowers the stability.

The object was therefore to remedy all of these disadvantages of the prior art. In particular, the aim was to make available products with reduced stickiness or greasiness. Products in the field of care cosmetics, decorative cosmetics and pharmacological technology were likewise to be freed from the described disadvantages of the prior art.

Furthermore, it was an object of the invention to develop cosmetic bases for cosmetic preparations which are characterized by good skin compatibility.

It was also an object of the present invention to provide product with the widest possible variety of applications. For example, the aim was to provide bases for preparation forms such as cleansing emulsions, face and bodycare preparations, but also, in particular, medicopharmaceutical application forms, for example preparations against acne and other skin conditions.

Surprisingly, we have found, and herein lies the basis to the attainment of the objects, that oil-in-water emulsions, in particular O/W microemulsions (a) comprising at least one emulsifier (emulsifier A), chosen from the group of emulsifiers having the following properties
their lipophilicity is either dependent on the pH inasmuch as an increase or decrease in pH results in an increase or decrease in lipophilicity, it being unimportant which of the two possibilities of change in the lipophilicity is effected by the increase or the decrease in the pH, and/or
their lipophilicity is dependent on the temperature inasmuch as the lipophilicity increases with increasing temperature and their hydrophilicity increases with decreasing temperature,
(b) also optionally further substances which are soluble or dispersible in the oil phase or the water phase, including, preferably, those chosen from the group of emulsifiers not covered by the definition of emulsifier A, in particular those which act primarily as W/O emulsifiers,
(c) an effective amount of shea butter, overcome the disadvantages of the prior art.

Shea butter (also: shea fat, karite fat, galam butter) is a natural solid obtained from the plant *Butyrospermum parkii*, the African shea butter tree and is available in commercial quantities. Usually, shea fat comprises 89 to 98% by weight of triglycerides, glycerol partial esters and free fatty acids, and a content of from 2 to 11% by weight of nonhydrolyzable fractions, of which hydrocarbons ("karitenes"), triterpene alcohols and sterols are the most important.

If the nonhydrolyzable fractions are alcohols, the majority are present in the form of cinnamic esters. Accordingly, the designation "nonhydrolyzable" for this fraction does not apply in the strict sense. From the overview literature on the theme of shea fat, reference may be made to the publications by Itoh et al. in Oleagineaux, 29,5, 253 (1974), Olberg et al. in Seifen-Öle-Fette-Wachse, 113, 10, 333 (1987) and Peers in J.Sci.Food Agric. 28, 1000 (1977).

Shea fat and shea fat fractions have been known in skincare for a long time for their care and protecting properties. The action of these fatty substances is attributed to an influencing of biochemical inflammation processes since the UV absorption in the UVA and UVB region is only weakly defined. Nevertheless, the prior art was unable to point the way to the present invention.

If phase inversion, within the meaning of the present invention, is essentially triggered by varying the temperature, O/W emulsions, in particular O/W microemulsions, are obtainable, where the size of the oil droplets is essentially determined by the concentration of the emulsifier(s) used, inasmuch as a higher emulsifier concentration brings about smaller droplets and a lower emulsifier concentration leads to relatively large droplets. If phase inversion is essentially triggered by varying the temperature, it is entirely advantageous to dispense with further emulsifiers not covered by the definition of emulsifier A, namely W/O emulsifiers.

According to the invention, cosmetic or dermatological preparations advantageously comprise 0.1 to 20% by weight, advantageously 0.5 to 10% by weight, very particularly preferably 1 to 5% by weight, of shea butter.

If phase inversion is essentially triggered by varying the pH, O/W emulsions, in particular O/W microemulsions are obtainable. If phase inversion is triggered essentially by varying the pH, it is entirely advantageous to use one or more further emulsifiers not covered by the definition of emulsifier A, namely W/O emulsifiers.

According to the invention, O/W microemulsions can be obtained if the oil phase fraction is less than about 20% by weight, in particular less than about 15% by weight, based on the overall weight of the preparation, if less than about 5% by weight of an additional W/O emulsifier not covered by the definition of the emulsifier A is present, and/or if the oil phase has a high proportion of polar oils.

According to the invention, O/W emulsions ("macroemulsions") can be obtained if less than about 5% by weight of an additional W/O emulsifier not covered by the definition of emulsifier A and more than about 20% by weight of a polar oil phase are present. Additional gel formers (e.g. carbopols, xanthan gum, cellulose derivatives) can advantageously be used.

In individual cases it is possible to slightly exceed or fall below the abovementioned concentration limits and nevertheless obtain the emulsion types in question. In view of the wide diversity of suitable emulsifiers and oil constituents, this is not unexpected for the person skilled in the art, so that he or she knows that such excesses or deficits do not depart from the basis of the present invention.

Where the phase inversion is initiated essentially by varying the temperature, O/W emulsions, especially O/W microemulsions, are obtainable, the size of the oil droplets being determined essentially by the concentration of the emulsifier or emulsifiers used, such that a higher emulsifier concentration produces smaller droplets and a lower emulsifier concentration leads to larger droplets. If phase inversion is triggered essentially by varying the temperature, it is entirely advantageous, although not absolutely necessary, to dispense with further emulsifiers not covered by the definition of emulsifier A, namely W/O emulsifiers.

If phase inversion is essentially triggered by varying the pH, O/W emulsions, in particular O/W microemulsions, and also O/W/O emulsions, are obtainable. If phase inversion is triggered essentially by varying the pH, it is entirely advantageous to use one or more further emulsifiers not covered by the definition of emulsifier A, namely W/O emulsifiers.

According to the invention, O/W microemulsions can be obtained if the oil phase fraction is less than about 20% by weight, in particular less than about 15% by weight, based on the overall weight of the preparation, if less than about 5% by weight of an additional W/O emulsifier which is not covered by the definition of emulsifier A is present, and/or if the oil phase has a high proportion of polar oils.

According to the invention, O/W emulsions ("macroemulsions") can be obtained if less than about 5% by weight of an additional W/O emulsifier not covered by the definition of emulsifier A and more than about 20% by weight of a polar oil phase are present. Additional gel formers (e.g. carbopols, xanthan gum, cellulose derivatives) can advantageously be used.

In individual cases it is possible to slightly exceed or fall below the abovementioned concentration limits and nevertheless obtain the emulsion types in question. In view of the wide diversity of suitable emulsifiers and oil constituents, this is not unexpected for the person skilled in the art, so that he or she knows that such excesses or deficits do not depart from the basis of the present invention.

Surprisingly, we have found that the pigment particle(s) used according to the invention are in the form of solids, and to a certain extent "encapsulated", namely separate from other constituents of the preparations, in some of which they can even have limited solubility. It is assumed that the solid particles of the sparingly soluble UV filter substances receive a coating film as a result of the incorporation process according to the invention, which film presumably comprises emulsifier molecules as essential constituent.

According to the invention the recrystallization of the s-triazine derivative(s) used according to the invention can be prevented. Moreover, light protection preparations are obtainable according to the invention which have excellent use properties.

FIG. 1 shows a very simplified representation of a phase diagram. The variable parameter P is plotted against the temperature $\theta$ as second variable. P is here a concentration parameter, either the proportion of the oil phase, the proportion of the water phase or the concentration of an emulsifier or an emulsifier mixture. For systems according to the invention it is the case that at relatively low temperatures an O/W emulsion is present and as the temperature increases the phase inversion range can be passed through. If the temperature is increased further, W/O emulsions are observed. The structure of the system in the phase inversion range is seemingly unimportant for the present invention. For example, it is conceivable that lamellar phases, bicontinuous phases, cubic, hexagonal or inverse hexagonal phases are present in the phase inversion range, and also that the phase inversion range is composed of two or more identical or more or less different phases.

The phase inversion range can be represented mathematically as a point quantity within the straight-line coordinate system $\Sigma$, which is formed by the parameters of temperature, the concentration of a suitable emulsifier or of an emulsifier mixture in the preparation and the respective concentrations of the oil phase and water phase, according to:

$$\Sigma = \{O, \theta, m, H, W\},$$

where
- $O$ = coordinate origin
- $\theta$ = temperature
- $m$ = concentration of the emulsifier/emulsifier mixture
- $H$ = concentration of the oil phase
- $W$ = concentration of the water phase.

Strictly speaking of course, in a multicomponent emulsifier system, the contribution $m_i$ of each individual emulsifier to the overall function must be taken into consideration which, in the case of an i-component emulsifier system, leads to the relationship $$\Sigma = \{O, \theta, m_1, m_2, \ldots, m_i, H, W\}.$$

The phase inversion range $\Phi$ here in the mathematical sense is a continuous region or a large number of continuous regions within the coordinate system $\Sigma$. $\Phi$ represents the total amount of coordinate points $K(\theta, a, m_1, m_2, \ldots, m_i, H, W)$, which determine mixtures according to the invention of a water phase of concentration W, oil phase of concentration H, i emulsifiers according to the invention of concentration $m_i$ at the temperature $\theta$, and for which, upon passing from a coordinate $K_1 \notin \Phi$ to a coordinate $K_2 \in \Phi$, phase inversion occurs, as described in FIG. 2.

It is irrelevant here whether the phase inversion range of a given system is a single coherent (i+3)-dimensional field or consists of two or more such fields which are coherent but separate from one another, i.e. corresponding to two or more phase inversion ranges of a given system. Within the scope of the disclosure presented herein, "the" or "a" phase inversion range is always generally referred to, even if two or more such ranges separate from one another are present.

The variable coordinates given in FIG. 2 are temperature $\theta$ and the above-described concentration parameter P, it being possible for which specific concentration parameter is involved to remain open. On passing from $K_1$ to $K_2$, only the temperature is increased, and the other variables are kept constant.

Under the conditions according to the invention, this process is not reversible, i.e. if the system reverts from the coordinate $K_2 \in \Phi$ to the coordinate $K_1 \notin \Phi$, transparent O/W microemulsions according to the invention may be obtained.

The practice of preparing a microemulsion according to the invention accordingly advantageously consists, after choosing suitable raw materials, i.e. water phase and oil phase, one or more O/W emulsifiers used according to the invention, the latter being present in concentrations at which phase inversion is possible for the given mixture, and optionally further substances, in combining the individual components with stirring, bringing about a phase inversion by increasing the temperature of the mixture, and thereafter allowing the mixture to cool to room temperature with continued stirring.

However, it is also possible here to vary two or more parameters at the same time, as shown in FIG. 3. In FIG. 3 the concentration of the water phase is plotted against the temperature. Starting from the coordinate $K_1 \notin \Phi$, by increasing the temperature, while maintaining all other parameters, the coordinates $K_2 \notin \Phi$ and $K_4 \notin \Phi$ can be reached, or $K_3 \in \Phi$. Starting from the coordinates $K_3$ and $K_4$, by lowering the temperature, while maintaining all other parameters, back to the coordinate $K_1$, O/W microemulsions according to the invention can be obtained.

Starting from the coordinates $K_3$ and $K_4$, by lowering the temperature, and by additionally varying the concentration of the oil phase, in FIG. 3 by the addition of water, the coordinate $K_5$ can be reached and O/W microemulsions according to the invention can be obtained.

In view of FIG. 3, it is logical that starting from the coordinate $K_4$, although this is outside the phase inversion range, systems similar to those which start from $K_3$ can be obtained, since starting from $K_4$ if the temperature is lowered, the phase inversion range must also automatically be traversed.

Also, starting from the coordinate $K_1$, by varying the concentration of the water phase, i.e. for example by adding water, as is shown in FIG. 3, the coordinate $K_5$ can be reached, and O/W microemulsions according to the invention can be obtained. In this regard, however, it must first be mentioned that in this case an O/W microemulsion according to the invention, to a certain extent as a concentrate, must already be present, which is then converted into an O/W microemulsion according to the invention of different composition by dilution.

However, having said all that, it was surprising and therefore involves independent inventive activity, that starting from the coordinate $K_2$, which lies outside the phase inversion range, either by simply varying the temperature back to the coordinate $K_1$ or by additionally varying the concentration of the oil phase, i.e., for example, by additional dilution with a water phase to the coordinate $K_5$, O/W microemulsions according to the invention are also obtainable without passing through phase inversion. This is advantageously effected by bringing a mixture of the base components, comprising water phase, oil phase, one or more of the O/W emulsifiers used according to the invention, if desired one or more W/O emulsifiers, and optionally further auxiliaries, additives and/or active ingredients, which form an O/W emulsion below the phase inversion temperature range, to a temperature at which the components which are soluble in the oil phase are present either in dissolved form or at least in the molten state and which corresponds at least to the melting temperature of the highest-melting oily component which is not present in the dissolved state, which is below the phase inversion temperature range of the system, and afterwards cooling the resulting O/W emulsion to room temperature to form an O/W microemulsion. This is preferably carried out with stirring.

This process according to the invention is particularly suitable if heat-sensitive or readily volatile substances are to be incorporated into the O/W microemulsions according to the invention. Moreover, this process, which is carried out at relatively low temperatures, is energy-saving compared with customary processes.

FIG. 4 describes the case in which no O/W emulsifier according to the invention is initially present in the coordinate $L_1$, and in which the system is brought to a coordinate $L_3 \notin \Phi$ or to a coordinate $L_2 \notin \Phi$ by increasing the temperature. The coordinate $L_2$ can of course also be achieved by cooling a system present in the coordinate $L_3$. The coordinates $L_2$ and $L_3$, in which, for example, W/O emulsions can be present, differ in principle merely by virtue of the fact that the temperature assigned to $L_3$ is higher than that temperature which can be assigned to the phase inversion temperature range.

The presence of an additional W/O emulsifier for systems which are symbolized in FIG. 4 is not necessarily required, but is advantageous. Addition of an O/W emulsifier according to the invention or of two or more such emulsifiers in the coordinates $L_2$ or $L_3$, on lowering the temperature, conveys the system to the coordinate $L_4$, at which an O/W microemulsion according to the invention is present.

A further advantageous embodiment of the process according to the invention accordingly consists, after choosing suitable raw materials, i.e. water phase and oil phase and optionally further substances, in bringing the individual components, with stirring, to a temperature at which phase inversion is possible for the given mixture and, by adding the O/W emulsifier used according to the invention or the O/W emulsifiers used according to the invention to the mixture, bringing about phase inversion, and afterwards allowing the mixture to cool to room temperature with continued stirring.

It is not beyond the ability of the person skilled in the art to determine, by simple experiments, the suitable temperature range within which a given mixture can pass through phase inversion. This temperature range is usually to be chosen between 70 and 95° C., but in an individual case can also be above or below this.

In practice, it is possible and in some cases even advantageous for the temperature range which can be assigned to the phase inversion range also to be exceeded during the preparation of a microemulsion according to the invention since this range will then automatically be traversed upon cooling to room temperature.

The practice of the preparation of an emulsion according to the invention advantageously consists, after choosing suitable raw materials, i.e. water phase and oil phase, one or more emulsifiers of type A, the latter being present in concentrations at which phase inversion is possible for the given mixture, and optionally further substances, in heating the individual components with stirring to a temperature at which phase inversion is possible for the given mixture, and, by increasing or decreasing the pH of the mixture, bringing about phase inversion, and afterwards allowing the mixture to cool to room temperature with continued stirring. One or more intermediate homogenization steps are advantageous, but are not absolutely necessary.

A further advantageous embodiment of the process according to the invention consists, after choosing suitable raw materials, i.e. water phase and oil phase, one or more emulsifiers of type A, the latter being present in concentrations at which phase inversion is possible for the given mixture, and optionally further substances, in bringing the individual components, with stirring, to a pH at which phase inversion is possible for the given mixture, and, by increasing the temperature of the mixture, bringing about phase inversion, and afterwards allowing the mixture to cool to room temperature with continued stirring. One or more intermediate homogenization steps are advantageous, but are not absolutely necessary.

A third advantageous embodiment of the process according to the invention consists, after choosing suitable raw materials, i.e. water phase and oil phase, one or more emulsifiers of type A and optionally further substances, in bringing the individual components, with stirring, to a pH and a temperature at which phase inversion is possible for the given mixture, and, by adding the emulsifier A or the emulsifiers A to the mixture, bringing about phase inversion, and afterwards allowing the mixture to cool to room temperature with continued stirring. One or more intermediate homogenization steps are advantageous, but are not absolutely necessary.

In practice, it is possible and in some cases even advantageous for the temperature range which can be assigned to the phase inversion range also to be exceeded during the preparation of an emulsion according to the invention since this range is then automatically traversed upon cooling to room temperature.

Cosmetic and dermatological preparations according to the invention comprise inorganic pigments, which are X-ray amorphous or non-X-ray amorphous, based on metal oxides and/or other metal compounds which are sparingly soluble or insoluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides. Particular preference is given to pigments based on $TiO_2$.

X-ray amorphous oxide pigments are metal oxides or semimetal oxides which reveal no or no recognizable crystal structure in X-ray diffraction experiments. Such pigments are often obtainable by flame reaction, for example by reacting a metal or semimetal halide with hydrogen and air (or pure oxygen) in a flame.

In cosmetic dermatological or pharmaceutical formulations, X-ray-amorphous oxide pigments are used as thickeners and thixotropic agents, flow auxiliaries, for emulsion and dispersion stabilization and as carrier substance (for example for increasing the volume of finely divided powders).

X-ray-amorphous oxide pigments which are known and are often used in cosmetic or dermatological technology are the silicon oxides of the Aerosil® grade (CAS No. 7631-86-9). Aerosils®, available from DEGUSSA, are characterized by low particle size (e.g. between 5 and 40 nm), where the particles are to be regarded as spherical particles of very uniform dimension. Macroscopically, Aerosils® are recognizable as loose, white powders. Within the meaning of the present invention, X-ray-amorphous silicon dioxide pigments are particularly advantageous and, of these, precisely those of the Aerosil® grade are preferred.

Advantageous Aerosil® grades are, for example, Aerosil® OX50, Aerosil® 130, Aerosil® 150, Aerosil® 200, Aerosil® 300, Aerosil® 380, Aerosil® MOX 80, Aerosil® MOX 170, Aerosil® COK 84, Aerosil® R 202, Aerosil® R 805, Aerosil® R 812, Aerosil® R 972, Aerosil® R 974, Aerosil® R976.

According to the invention, cosmetic or dermatological light protection preparations advantageously comprise 0.1 to 20% by weight, advantageously 0.5 to 10% by weight, very particularly preferably 1 to 5% by weight, of X-ray-amorphous oxide pigments.

According to the invention, the non-X-ray-amorphous inorganic pigments are advantageously present in hydrophobic form, i.e. they have been surface-treated to repel water. This surface treatment can involve providing the pigments with a thin hydrophobic layer by methods known per se.

Such a method consists, for example, in producing the hydrophobic surface layer according to a reaction as in

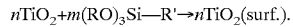

n and m are stoichiometric parameters to be used as desired, and R and R' are the desired organic radicals. Hydrophobicized pigments prepared as in DE-A 33 14 742, for example, are advantageous.

Advantageous $TiO_2$ pigments are available, for example, under the trade names T 805 from Degussa.

The total amount of inorganic pigments, in particular hydrophobic inorganic micropigments, in the finished cosmetic or dermatological preparations is advantageously chosen from the range 0.1–30% by weight, preferably 0.1–10.0% by weight, based on the total weight of the preparations.

The emulsifiers A are preferably chosen from the group of emulsifiers which are good proton donors or proton acceptors, it having to be ensured that either their lipophilicity is dependent on the pH inasmuch as an increase or decrease in the pH results in an increase or decrease in lipophilicity, it being unimportant which of the two possibilities of change in the lipophilicity is effected by the increase or the decrease in the pH, or their lipophilicity is dependent on the temperature inasmuch as the lipophilicity increases with increasing temperature, and their hydrophilicity increases with decreasing temperature, or their lipophilicity is dependent on pH and temperature inasmuch as an increase or decrease in pH results in an increase or decrease in lipophilicity, it being unimportant which of the two possibilities of change in the lipophilicity is effected by the increase or the decrease in the pH, and inasmuch as the lipophilicity increases with increasing temperature and their hydrophilicity increases with decreasing temperature.

The emulsifiers of type A are advantageously chosen from the group of sorbitaar esters and sucrose esters, in particular branched and unbranched alkyl esters and alkenyl esters having carbon chains of 4–24 carbon atoms, preferably sorbitan stearate, sorbitan oleate, glyceryl sorbitan stearate, sucrose monostearate, sucrose minolaurate, sucrose palmitate.

The emulsifiers of type A can advantageously be chosen from the group of monoglycerol monocarboxylic monoesters, in particular those characterized by the structures

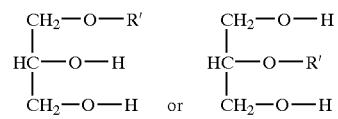

where R' is a branched or unbranched acyl radical having 6–14 carbon atoms. R' is advantageously chosen from the group of unbranched acyl radicals.

The acids on which these esters are based are

| hexanoic acid | (caproic acid) | (R' = —$C_5H_{11}$), |
|---|---|---|
| heptanoic acid | (enanthic acid) | (R' = —$C_6H_{13}$), |
| octanoic acid | (caprylic acid) | (R' = —$C_7H_{15}$), |
| nonanoic acid | (pelargonic acid) | (R' = —$C_8H_{17}$), |
| decanoic acid | (capric acid) | (R' = —$C_9H_{19}$), |
| undecanoic acid | | (R' = —$C_{10}H_{21}$), |
| 10-undecenoic acid | (undecylenic acid) | (R' = —$C_{10}H_{19}$), |
| dodecanoic acid | (lauric acid) | (R' = —$C_{11}H_{23}$), |
| tridecanoic acid | | (R' = —$C_{12}H_{25}$), |
| tetradecanoic acid | (myristic acid) | (R' = —$C_{13}H_{27}$). |

R' particularly advantageously represents the octanoyl radical (capryiic acid radical) or the decanoyl radical (capric acid radical), and is therefore represented by the formulae R'=—$C_7H_{15}$ or R'=—$C_9H_{19}$.

The emulsifiers of type A can also be advantageously chosen from the group of di- and triglycerol monocarboxylic monoesters. According to the invention, the di- or triglycerol units of the diglycerol monocarboxylic monoesters or triglycerol monocarboxylic monoesters according to the invention are in the form of linear, unbranched molecules, i.e. "monoglycerol molecules" etherified via the respective OH groups in the 1- or 3-position.

A low proportion of cyclic di- or triglycerol units, and glycerol molecules etherified via the OH groups in the 2-position can be tolerated. It is, however, advantageous to keep such impurities as low as possible.

The monocarboxylic monoesters according to the invention are preferably characterized by the following structure:

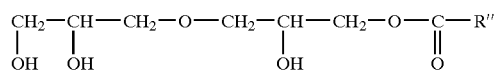

where R" is a hydrocarbon radical, advantageously a branched or unbranched alkyl or alkenyl radical having 5 to 17 carbon atoms.

The monocarboxylic esters of triglycerol according to the invention are preferably characterized by the following structure:

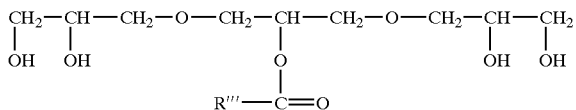

where R'" is a hydrocarbon radical, advantageously a branched or unbranched alkyl or alkenyl radical having 5 to 17 carbon atoms.

The acids on which these esters are based are

| hexanoic acid | (caproic acid) | (R" and R'" = —$C_5H_{11}$), |
|---|---|---|
| heptanoic acid | (enanthic acid) | (R" and R'" = —$C_6H_{13}$), |
| octanoic acid | (caprylic acid) | (R" and R'" = —$C_7H_{15}$), |
| nonanoic acid | (pelargonic acid) | (R" and R'" = —$C_8H_{17}$), |
| decanoic acid | (capric acid) | (R" and R'" = —$C_9H_{19}$), |
| undecanoic acid | | (R" and R'" = —$C_{10}H_{21}$), |
| 10-undecenoic acid | (undecylenic acid) | (R" and R'" = —$C_{10}H_{19}$), |
| dodecanoic acid | (lauric acid) | (R" and R'" = —$C_{11}H_{23}$), |
| tridecanoic acid | | (R" and R'" = —$C_{12}H_{25}$), |
| tetradecanoic acid | (myristic acid) | (R" and R'" = —$C_{13}H_{27}$), |
| pentadecanoic acid | | (R" and R'" = —$C_{14}H_{29}$), |
| hexadecanoic acid | (palmitic acid) | (R" and R'" = —$C_{15}H_{31}$), |
| heptadecanoic acid | (margaric acid) | (R" and R'" = —$C_{16}H_{33}$), |
| octadecanoic acid | (stearic acid) | (R" and R'" = —$C_{17}H_{35}$). |

R" and R'" are particularly favorably chosen from the group of unbranched alkyl radicals having an uneven number of carbon atoms, in particular 9, 11 and 13 carbon atoms.

In general, the monocarboxylic monoesters of diglycerol are preferable to those of triglycerol.

According to the invention, very particular preference is given to

| diglycerol monocaprate | (DMC) | R" = 9 |
|---|---|---|
| triglycerol monolaurate | (TML) | R'" = 11 |
| diglycerol monolaurate | (DML) | R" = 11 |
| triglycerol monomyristate | (TMM) | R'" = 13 |

A preferred monocarboxylic monoester of diglycerol according to the invention which has proven successful is diglycerol monocaprate (DMC).

In an advantageous embodiment of the present invention, an additional content of di- or triglycerol esterified in different positions is used, as is, where appropriate, a content of the various diesters of di- or triglycerol.

Also advantageous are triglyceryl diisostearate (nomenclature according to CTFA: polyglyceryl-3 dilsostearate), isostearyldiglyceryl succinate, diglyceryl sesquiisostearate (nomenclature according to CTFA: polyglyceryl-2 sesquiisostearate), triglyceryl polyhydroxystearate (nomenclature according to CTFA: polyglyceryl-2 polyhydroxystearate).

Cetearyl isononanoate, dicocoylpentaerythrityldistearyl citrate, and also the methicone copolyols, cyclomethicone copolyols, alkylmethicone copolyols, in particular laurylmethicone copolyol, cetyldimethicone copolyol, have also proven advantageous according to the invention.

The emulsifier(s) of type A is/are particularly advantageously chosen from the group of branched or unbranched alkylmonocarboxylic acids, alkenylmonocarboxylic acids and alkylenedicarboxylic acids having 4 to 30 carbon atoms, in particular stearic acid, oleic acid, succinic acid, hexanoic acid (caproic acid), heptanoic acid (enanthic acid), octanoic acid (caprylic acid), nonanoic acid (pelargonic acid), decanoic acid (capric acid), undecanoic acid, undecenoic acid (undecylenic acid), dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), isostearic acid, behenic acid. It is also advantageous to choose the emulsifiers A from the group of cosmetically or pharmaceutically acceptable salts of the abovementioned carboxylic acids, in particular the alkali metal, ammonium, monoalkylammonium, dialkylammonium, trialkylammonium and tetraalkylammonium salts.

The emulsifier(s) A is/are likewise particularly advantageously chosen from the group of mono-, oligo- and polyethoxylated compounds, in particular polyethoxylated mono- or polybasic alcohols or fatty acids, for example ceteareth-20, PEG-20 glyceryl stearate, steareth-20, PEG-20 stearate, PEG-30 stearate, PEG-40 castor oil, PEG-1 glycerol sorbitan oleostearate, PEG-7 hydrogenated castor oil, PEG-40 sorbitan peroleate, PEG-45 dodecyl glycol copolymer.

The emulsions according to the invention advantageously comprise the emulsifier A or the emulsifiers A in concentrations of 0.01–20% by weight, preferably 0.05–10% by weight, particularly preferably 0.1–5% by weight, in each case based on the total weight of the composition.

According to the invention, it is possible to multiply the use amounts of UV filters which are themselves sparingly soluble or insoluble in oil components, in particular tris(2-ethylhexyl) 4,4',4"-(1,3,5-triazine-2,4,6-triyltriimino)trisbenzoate, but also 2-phenylbenzimidazole-5-sulfonic acid or salts thereof in cosmetic or dermatological preparations compared with the prior art.

The total amount of UV filter substances which are themselves sparingly soluble in oil components, in particular tris(2-ethylhexyl) 4,4',4"-(1,3,5-triazine-2,4,6-triytriimino)trisbenzoate, but also 2-phenylbenzimidazole-5-sulfonic acid and salts thereof in the finished cosmetic or dermatological preparations is advantageously chosen from the range 0.1–10.0% by weight, preferably 0.5–6.0% by weight, based on the total weight of the preparations.

It is advantageous according to the invention to use additional oil-soluble UVA filters and/or UVB filters in the lipid phase and/or water-soluble UVA filters and/or UVB filters in the aqueous phase in the preparations according to the invention.

The light protection formulations according to the invention can advantageously comprise further substances which absorb UV radiation in the UVB region, the total amount of filter substances being, for example, 0.1% by weight to 30% by weight, preferably 0.5 to 10% by weight, in particular 1 to 6% by weight, based on the total weight of the preparations, in order to make available cosmetic preparations which protect the skin from the entire range of ultraviolet radiation.

The additional UVB filters can be oil-soluble or water-soluble. Examples of advantageous oil-soluble UVB filter substances are:

- 3-benzylidenecamphor derivatives, preferably 3-(4-methylbenzylidene)camphor, 3-benzylidenecamphor;
- 4-aminobenzoic acid derivatives, preferably 2-ethylhexyl 4-(dimethyl-amino)benzoate, amyl 4-(dimethylamino)benzoate;
- esters of cinnamic acid, preferably 2-ethylhexyl 4-methoxycinnamate, isopentyl 4-methoxycinnamate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably di(2-ethylhexyl) 4-methoxybenzalmalonate;
- tris(2-ethylhexyl) 4,4',4"-(1,3,5-triazine-2,4,6-triyltriimino)trisbenzoate.

Examples of advantageous water-soluble UVB filter substances are:

- salts of 2-phenylbenzimidazole-5-sulfonic acid, such as its sodium, potassium or its triethanolammonium salt, and the sulfonic acid itself,
- sulfonic acid derivatives of benzophenones, preferably 2-hydroxy-4-methoxybenzophenone-5-sulfonic acid and salts thereof,
- sulfonic acid derivatives of 3-benzylidenecamphor, such as, for example, 4-(2-oxa-3-bornylidenemethyl)benzenesulfonic acid, 2-methyl-5-(2-oxo-3-bornylidene-methyl)sulfonic acid and salts thereof.

The list of said UVB filters which can be used in combination with the active ingredient combinations according to the invention is not of course intended to be limiting.

It can also be advantageous to use additional UVA filters in the preparations according to the invention which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)-propane-1,3-dione. These combinations and preparations which comprise these combinations are also provided by the invention. The amounts which can be used are those used for the UVB combination.

The cosmetic and/or dermatological light protection formulations according to the invention can have the customary composition and be used for cosmetic and/or dermatological light protection, and also for the treatment, care and cleansing of skin and/or hair and as a make-up product in decorative cosmetics.

For use, the cosmetic and dermatological preparations according to the invention are applied to the skin and/or hair in sufficient amount and in the manner conventional for cosmetics.

Particularly preferred cosmetic and dermatological preparations are those which are in the form of a sunscreen. Advantageously, these can additionally comprise at least one further UVA filter and/or at least one further UVB filter and/or at least one inorganic pigment, preferably an inorganic micropigment.

The cosmetic and dermatological preparations according to the invention can comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological formulation, such as alcohols, polyols, polymers, foam stabilizers, electrolytes, organic solvents or silicone derivatives.

An additional content of antioxidants is generally preferred. According to the invention, favorable antioxidants which can be used are all antioxidants suitable or conventional for cosmetic and/or dermatological applications.

It is also advantageous to add antioxidants to the preparations according to the invention. The antioxidants are advantageously selected from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active substances which are suitable according to the invention.

The amount of the abovementioned antioxidants (one or more compounds) in the preparations is preferably from 0.001 to 30% by weight, particularly preferably from 0.05 to 20% by weight, especially 1–10% by weight, based on the total weight of the preparation.

If vitamin E and/or derivatives thereof are used as the antioxidant or antioxidants, their respective concentrations are advantageously chosen from the range of 0.001–10% by weight, based on the total weight of the formulation.

If vitamin A or vitamin A derivatives or carotenes or derivatives thereof are used as the antioxidant or antioxidants, their respective concentrations are advantageously chosen from the range of 0.001–10% by weight, based on the total weight of the formulation.

The lipid phase can advantageously be chosen from the following group of substances:

mineral oils, mineral waxes oils, such as triglycerides of capric or caprylic acid, but preferably castor oil;

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alkyl benzoates;

silicone oils such as dimethylpolysiloxanes, diethylpolysiloxanes, diphenylpolysiloxanes and mixtures thereof.

For the purposes of the present invention, the oil phase of the emulsions, oleogels and hydrodispersions or lipodispersions is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group consisting of esters of aromatic carboxylic acids and saturated and/or unsaturated, branched and/or unbranched alcohols having a chain length of from 3 to 30 carbon atoms. Such ester oils can advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethyihexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, e.g. jojoba oil.

The oil phase can also advantageously be chosen from the group of branched and unbranched hydrocarbons and hydrocarbon waxes, silicone oils, dialkyl ethers, from the group of saturated or unsaturated, branched or unbranched alcohols, and also fatty acid triglycerides, namely the triglycerol esters of saturated and/or unsaturated, branched and/or unbranched alkanecarboxylic acids of a chain length from 8 to 24, in particular 12–18, carbon atoms. The fatty acid triglycerides can advantageously be chosen, for example, from the group of synthetic, semisynthetic and natural oils, e.g. olive oil, sunflower oil, soybean oil, peanut oil, rapeseed oil, almond oil, palm oil, coconut oil, palm kernel oil and the like.

For the purposes of the present invention, any mixtures of such oil and wax components can also advantageously be used. When required, it can also be advantageous to use waxes, for example cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

Of the hydrocarbons, paraffin oil, squalane and squalene are advantageously to be used for the purposes of the present invention.

The oil phase can advantageously also contain cyclic or linear silicone oils or can consist entirely of such oils, although it is preferable to use an additional content of other oil phase components in addition to the silicone oil or silicone oils.

Cyclomethicone (octamethylcyclotetrasiloxane) is advantageously the silicone oil to be used according to the invention. However, other silicone oils can also advantageously be used for the purposes of the present invention, for example hexamethylcyclotrisiloxane, polydimethylsiloxane, poly(methylphenylsiloxane).

Mixtures of cyclomethicone and isotridecyl isononanoate and mixtures of cyclomethicone and 2-ethylhexyl isostearate are particularly advantageous.

The aqueous phase of the preparations according to the invention may advantageously comprise alcohols, diols or polyols of low carbon number, and also their ethers, preferably ethanol, isoprbpanol, propyleine glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol, and especially one or more thickeners which can advantageously be chosen from the group consisting of silicon dioxide, aluminum isilicates and polysaccharides and derivatives thereof, e.g. hyaluronic acid, xanthan gum, hydroxypropylmethylcellulose, and particularly advantageously from the group of polyacrylates, preferably a polyacrylate from the group consisting of the so-called carbopols, for example carbopol grades 980, 981, 1382, 2984, 5984, in each case individually or in combination.

The text below briefly discusses some peculiarities and differences in the prerequisites of O/W emulsions and O/W microemulsions according to the invention.

Oils and fats differ inter alia in their polarity, which is difficult to define. It has already been proposed to adopt the interfacial tension with respect to water as a measure of the polarity index of an oil or an oil phase. In this case, the lower the interfacial tension between this oil phase and water, the greater the polarity of the oil phase in question. According to the invention, the interfacial tension is to be regarded as one possible measure of the polarity of a given oil component.

The interfacial tension is that force which acts on an imaginary line one meter in length located in the interface between two phases. The physical unit of this interfacial tension is conventionally calculated from the force/length relationship and is usually expressed in mN/m (millinewtons divided by meters). It has a positive sign if it endeavors to reduce the interface. In the converse case, it has a negative sign.

According to the invention, the limit below which an oil phase is "polar" and above which an oil phase is "nonpolar" is regarded as 30 mN/m.

According to the invention, the oil phase is advantageously chosen for O/W microemulsions from the group of polar oil components which have a polarity between 10 and 30 mN/m, where it must be ensured that at least one nonpolar oil component is present.

Advantageous O/W microemulsions are obtained if the oil phase is chosen from the group of polar oil components, particularly preferably from the group of natural, synthetic or semisynthetic oil components, which have a polarity between 10 and 20 mN/m, where it must be ensured that at least one nonpolar oil component is present.

It is also advantageous to use polar vegetable oils as polar oils of the O/W emulsions according to the invention. The vegetable oils can advantageously be chosen from the group of oils from the plant families Euphorbiaceae, Poaceae, Fabaceae, Brassicaceae, Pedalaceae, Asteraceae, Linaceae, Flacourticaceae, Violales, preferably chosen from the group consisting of natural castor oil, wheatgerm oil, grapeseed oil, kukui nut oil, safflower oil, thistle oil, oil of evening primrose and further oils which comprise at least 1.5% by weight of linoleic acid glycerides.

The addition of electrolytes brings about a change in the solubility behavior of a hydrophilic emulsifier. The hydrophilic emulsifiers having the structures or properties described above pass through a partial phase inversion, leading to solubilization of water by the oil phase, which results in a stable microemulsion.

The microemulsions according to the invention therefore advantageously comprise electrolytes, in particular one or more salts containing the following anions: chlorides, and also inorganic oxo element anions, and of these in particular sulfates, carbonates, phosphates, borates and aluminates. Electrolytes based on organic anions can also advantageously be used, for example lactates, acetates, benzoates, propionates, tartrates, citrates and many others. Comparable effects can also be achieved by ethylenediaminetetraacetic acid and salts thereof.

Cations of the salts which are preferably used are ammonium, alkylammonium, alkali metal, alkaline earth metal, magnesium, iron and zinc ions. It goes without saying that only physiologically acceptable electrolytes are to be used in cosmetics. On the other hand, specific medicinal applications of the microemulsions according to the invention may, at least in principle, require the use of electrolytes which should not be used without medical supervision.

Particular preference is given to potassium chloride, sodium chloride, magnesium sulfate, zinc sulfate and mixtures thereof. Also advantageous are salt mixtures as occur in the natural salt from the Dead Sea.

The concentration of the electrolyte or of the electrolytes should be about 0.01–10.0% by weight, particularly advantageously about 0.03–8.0% by weight, based on the total weight of the preparation.

The emulsifiers of type A are commonly regarded as O/W emulsifiers. A content of about 5–10% by weight of customary W/O emulsifiers advantageously promotes the formation of O/W/O emulsions, and a content of significantly more than 10% by weight of such emulsifiers leads to destabilization of the O/W/O emulsions.

If desired, for the preparation of O/W/O emulsions according to the invention, it is also advantageous to use hydrophilic and/or lipophilic gel formers. Although these do not generally contribute to the formation of multiple droplets, they promote the stability of multiple droplets once they have formed.

If, in a preparation process for O/W/O emulsions according to the invention, the pH is to be varied in order to bring an otherwise predetermined system into the phase inversion range, then it is advantageous to initially use the lowest possible electrolyte concentration in the water phase at the start of the process, and if possible to initially dispense with such a concentration entirely. It is also advantageous to introduce emulsifier A into the oil phase, for example for stearic acid in the concentration range 0.5–5% by weight, in particular 2% by weight. The presence of emulsifier which is not covered by the definition of emulsifier A is advantageously in the concentration range from about 5–10% by weight, in particular about 7% by weight.

The pH should advantageously only be varied once the W/O emulsion has formed, for example by the addition of NaOH.

In this respect, it is within the general knowledge of the person skilled in the art and requires no inventive activity to determine the temperature and pH range in which phase inversion takes place for a given emulsifier or a given emulsifier system in a given water/oil phase system. As a general guideline for the PIT at customary emulsifier concentrations, a temperature range of about 40–90° C. can be stated. In general, the PIT decreases as the emulsifier concentration increases.

If desired, during this process, the basic substances, auxiliaries, additives and/or active ingredients customary in cosmetics or medicinal galenics can also be added. It is clear to the person skilled in the art at which point in time such substances can be added to the process without the properties of the emulsion to be achieved being considerably impaired.

The examples below serve to outline the essence of the present invention in more detail without limiting the invention.

EXAMPLE 1

|  | % by weight |
|---|---|
| Glycerol | 5.00 |
| Mineral oil | 5.00 |
| Glyceryl stearate, ceteareth-20, ceteareth-12, cetylstearyl alcohol, cetyl palmitate | 3.50 |
| $C_{12-15}$-alkyl benzoate | 3.00 |
| Microcrystalline wax (Cera microcristallina), mineral oil (Paraffinum liquidum) | 3.00 |
| Ceteareth-20 | 1.50 |
| Shea butter | 1.00 |
| DMDM hydantoin | 0.40 |
| Perfume, dyes, preservatives | q.s. |
| Water | ad 100.00 |

The constituents of the oil phase are combined, as a result of which the mixture homogenizes, then combined with the water phase and brought to a temperature of 80–85° C. (i.e. into the phase inversion temperature range of the system), then cooled to room temperature (i.e. brought out of the phase inversion temperature range of the system again).

EXAMPLE 2

| | % by weight |
|---|---|
| Glycerol | 5.00 |
| Mineral oil | 5.00 |
| Glyceryl stearate, ceteareth-20, ceteareth-12, cetylstearyl alcohol, cetyl palmitate | 3.50 |
| $C_{12-15}$-alkyl benzoate | 3.00 |
| Microcrystalline wax (Cera microcristallina), mineral oil (Paraffinum liquidum) | 3.00 |
| Ceteareth-20 | 1.50 |
| Shea butter | 1.00 |
| Phenyltrimethicone | 1.00 |
| DMDM hydantoin | 0.40 |
| Perfume, dyes, preservatives | q.s. |
| Water | ad 100.00 |

The constituents of the oil phase are combined, as a result of which the mixture homogenizes, then combined with the water phase and brought to a temperature of 80–85° C. (i.e., into the phase inversion temperature range of the system), then cooled to room temperature (i.e. brought out of the phase inversion temperature range of the system again).

EXAMPLE 3

| | % by weight |
|---|---|
| Glycerol | 5.00 |
| Glyceryl stearate, ceteareth-20, ceteareth-12, cetylstearyl alcohol, cetyl palmitate | 3.70 |
| Phenyltrimethicone | 3.00 |
| Mineral oil (Paraffinum liquidum) | 3.00 |
| Dicaprylyl ether | 2.50 |
| $C_{12-15}$-akyl benzoate | 2.50 |
| Microcrystalline wax (Cera microcristallina), mineral oil (Paraffinum liquidum) | 2.00 |
| Cetearyl isononanoate | 1.50 |
| Ceteareth-20 | 1.30 |
| Shea butter | 0.75 |
| DMDM hydantoin | 0.40 |
| Perfume, dyes, preservatives | q.s. |
| Water | ad 100.00 |

The constituents of the oil phase are combined, as a result of which the mixture homogenizes, then combined with the water phase and brought to a temperature of 80–85° C. (i.e. into the phase inversion temperature range of the system), then cooled to room temperature (i.e. brought out of the phase inversion temperature range of the system again).

EXAMPLE 4

| | % by weight |
|---|---|
| Glycerol | 5.00 |
| Mineral oil | 5.00 |
| Glyceryl stearate, ceteareth-20, ceteareth-12, cetylstearyl alcohol, cetyl palmitate | 3.50 |
| $C_{12-15}$-alkyl benzoate | 3.00 |
| Microcrystalline wax (Cera microcristallina), mineral oil (Paraffinum liquidum) | 3.00 |
| phenyltrimethicone | 2.00 |
| Ceteareth-20 | 1.50 |
| Shea butter | 1.00 |
| DMDM hydantoin | 0.40 |
| Perfume, dyes, preservatives | q.s. |
| Water | ad 100.00 |

The constituents of the oil phase are combined, as a result of which the mixture homogenizes, then combined with the water phase and brought to a temperature of 80–85° C. (i.e. into the phase inversion temperature range of the system), then cooled to room temperature (i.e. brought out of the phase inversion temperature range of the system again).

EXAMPLE 5

| | % by weight |
|---|---|
| Glycerol | 5.00 |
| Mineral oil | 4.00 |
| Glyceryl stearate, ceteareth-20, ceteareth-12, cetylstearyl alcohol, cetyl palmitate | 3.70 |
| Dicaprylyl ether | 2.50 |
| $C_{12-15}$-Alkylbenzoate | 2.50 |
| Microcrystalline wax (Cera microcristallina), mineral oil (Paraffinum liquidum) | 2.50 |
| Phenyltrimethicone | 1.50 |
| Cetylstearyl isononanoate | 1.50 |
| Ceteareth-20 | 1.30 |
| Shea butter | 0.75 |
| DMDM hydantoin | 0.40 |
| Perfume, dyes, preservatives | q.s. |
| Water | ad 100.00 |

The constituents of the oil phase are combined, as a result of which the mixture homogenizes, then combined with the water phase and brought to a temperature of 80–85° C. (i.e. into the phase inversion temperature range of the system), then cooled to room temperature (i.e. brought out of the phase inversion temperature range of the system again).

EXAMPLE 6

| | % by weight |
|---|---|
| Glycerol | 5.00 |
| Mineral oil | 5.00 |
| Glyceryl stearate, ceteareth-20, ceteareth-12, cetylstearyl alcohol, cetyl palmitate | 3.50 |
| Shea butter | 3.00 |
| $C_{12-15}$-alkylbenzoate | 3.00 |
| Microcrystalline wax (Cera microcristallina), mineral oil (Paraffinum liquidum) | 3.00 |
| Ceteareth-20 | 1.50 |
| DMDM hydantoin | 0.40 |
| Perfume, dyes, preservatives | q.s. |
| Water | ad 100.00 |

The constituents of the oil phase are combined, as a result of which the mixture homogenizes, then combined with the water phase and brought to a temperature of 80–85° C. (i.e. into the phase inversion temperature range of the system), then cooled to room temperature (i.e. brought out of the phase inversion temperature range of the system again).

EXAMPLE 7

| | % by weight |
|---|---|
| $C_{12-15}$-alkyl benzoate | 4.50 |
| Glyceryl stearate, ceteareth-20, ceteareth-12, cetylstearyl alcohol, cetyl palmitate | 3.50 |
| Mineral oil (Paraffinum liquidum) | 3.50 |
| Shea butter | 3.00 |
| Microcrystalline wax (Cera microcristallina), mineral oil (Paraffinum liquidum) | 3.00 |
| Glycerol | 2.50 |
| Ceteareth-20 | 1.50 |
| DMDM hydantoin | 0.40 |
| Perfume, dyes, preservatives | q.s. |
| Water | ad 100.00 |

The constituents of the oil phase are combined, as a result of which the mixture homogenizes, then combined with the water phase and brought to a temperature of 80–85° C. (i.e. into the phase inversion temperature range of the system), then cooled to room temperature (i.e. brought out of the phase inversion temperature range of the system again).

What is claimed is:

1. An oil-in water microemulsion comprising an oil phase and a water phase and:
    (a) at least one emulsifier (emulsifier A), chosen from the group consisting of emulsifiers having the following properties
        their lipophilicity is either dependent on the pH inasmuch as an increase or decrease in pH results in an increase or decrease in lipophilicity, it being unimportant which of the two possibilities of change in the lipophilicity is effected by the increase or the decrease in the pH, and/or
        their lipophilicity is dependent on the temperature inasmuch as the lipophilicity increases with increasing temperature and their hydrophilicity increases with decreasing temperature.
    (b) optionally further comprising substances which are soluble or dispersible in the oil phase or the water phase,
    (c) an effective amount of shea butter to reduce stickiness/greasiness of the oil-in-water emulsion which comprises 0.5% to 10% by weight of shea butter.

2. The oil-in-water microemulsion of claim 1, wherein the emulsifier A is present in concentration of 0.05–10% by weight based an the total weight of the composition.

3. The oil-in-water microemulsion of claim 1, wherein the emulsifier A is present in concentration of 0.1–5% by weight based on the total weight of the composition.

4. The oil-in-water microemulsion of claim 1, which comprises 1% /to 5% by weight of shea butter.

5. The oil-in-water microemulsion of claim 1 wherein the substances of (b) are emulsifiers which are not covered by the definition of emulsifier A.

6. The oil-in-water microemulsion of claim 5 wherein the emulsifiers which are not covered by the definition of emulsifier A are oil-in-water-emulsifiers.

* * * * *